United States Patent [19]
Patch

[11] Patent Number: 6,084,936
[45] Date of Patent: Jul. 4, 2000

[54] ALMOST-EVERYWHERE EXTRAPOLATION FROM CONE-BEAM DATA

[75] Inventor: Sarah Kathryn Patch, Saratoga Springs, N.Y.

[73] Assignee: General Electric Company, Schenectady, N.Y.

[21] Appl. No.: 09/113,841

[22] Filed: Jul. 10, 1998

[51] Int. Cl.[7] .................................................. A61B 6/03
[52] U.S. Cl. ............................................. 378/4; 378/901
[58] Field of Search ................................ 378/4, 15, 99; 382/131

[56] References Cited

U.S. PATENT DOCUMENTS 5,598,453   1/1997   Baba et al. ............................... 378/146

OTHER PUBLICATIONS

Fritz John, "The Ultrahyperbolic Differential Equation with 4 Independent Variables", Duke Math. Journal, pp. 300–322, (1938).

Leifur Asgeirsson, "Ueber eine Mittelwertseigenschaft von Loesungen Homogener Linearer Partieller Differentialgleichungen Zweiter: Ordnung mit Konstanten Koeffizienten", Mathematische Annalen, 13, pp. 321–346 (1938).

Glynn Owens, "An Explicit Formula for the Solution of the Ultrahyperbolic Equation in Four Variables", Duke Math Journal, 9, pp. 272–282, (1942).

*Primary Examiner*—David Vernon Bruce
*Attorney, Agent, or Firm*—Donald S. Ingraham; Douglas E. Stoner

[57] ABSTRACT

A source applies imaging energy that passes through an object being imaged and is then detected by a detector. A scanning trajectory causes the detector to provide a Cauchy data set of measured cone beam data to a processor. The processor extrapolates by use of John's equation such that missing cone beam data is determined. The measured cone beam data and the determined cone beam data together provide a complete data set for exact image reconstruction.

20 Claims, 3 Drawing Sheets

ALMOST-EVERYWHERE EXTRAPOLATION FROM CONE-BEAM DATA

BACKGROUND OF THE INVENTION

This invention relates to X-ray imaging techniques, and, more particularly, to computerized tomography X-ray imaging using a minimal set of cone beam data measurements.

Computerized tomography (CT) uses a source of imaging energy such as X-ray energy and a detector for detecting imaging energy that has passed through an object of interest, often a patient being imaged for medical purposes. Typically, a single point source is used with an area detector such as an X-ray detector array.

Relative movement between the source, object of interest, and detector is used to collect data for image reconstruction purposes. Usually the source is moved, while the object and detector remain stationary relative to each other.

Typical source trajectories are "1 dimensional manifolds" described by parametric equations of a single variable. The advent of area X-ray detectors permits measurement of a 2 dimensional data set for each source position, since the detector lies in a 2 dimensional plane. Therefore, it is possible to measure a 1+2=3 dimensional data set of line integrals of the object being imaged.

This dimensional count is encouraging for volumetric imaging such as CT because the imaging object lies in three spatial dimensions. More specifically, complete CT data for a family of parallel planes constitutes a 2+1=3 dimensional data set and completely determines the imaging object.

Unfortunately, cone beam data generated by a single point source does not permit such simple reconstruction. A single circular trajectory does not provide a complete data set for Radon reconstruction (i.e., apart from measurement and discretization errors). Therefore, various scan trajectories have been used.

Among scan trajectories are those disclosed in U.S. Pat. No. 5,465,283 issued Nov. 7, 1995 to Tam. That patent discloses, among other information, the use of a scan trajectory of two offset circular scans with a line extending between them.

Generally, the scan trajectories result from relative movement among the source, detector, and object being imaged. Usually, the source is moved in a path about the object to define the scan trajectory. The object being imaged is often a medical patient, but could also be an industrial part being imaged to locate possible defects. When the object being imaged is an industrial part, the scan trajectory may be defined at least partly by movement of the object relative to the source and/or relative to the detector. A scan trajectory might also be defined at least partly by movement of the detector.

Such scan trajectories that provide complete cone beam data may present a number of problems. The path or paths followed by the source or other component being moved may be complex. This requires a complex robotic function. Additionally, the scan time for obtaining a complete data set may be longer than desirable. Especially in the case where the imaged object is a patient, it is desirable to limit the time and dose of X-ray exposure. A complex scan path requires a longer time of exposure than a simple path. Yet, if the dose is reduced to partially compensate for a long exposure time, the signal to noise ratio is reduced. Errors in the data, particularly due to lag and signal to noise degradation with decreasing dose, often are more troublesome with complex scan paths. Further, a complex scan path increases the amount of measured data and this in turn increases computational demands when using the reconstruction process to provide an image.

Although it is possible to provide image reconstruction with a incomplete data set, such a reconstructed image will be quite inexact, if not undetermined, in some regions as a result of not having the missing data.

BRIEF SUMMARY OF THE INVENTION

In an exemplary embodiment of the method of the invention, an object is imaged by applying imaging energy from a source to the object. Imaging energy that has passed through the object is detected by a detector. The object is scanned with the imaging energy such that the detector collects measured image data that constitutes a Cauchy data set for John's equation. Cauchy data sets and John's equations are known mathematic concepts. Briefly, a Cauchy data set allows one to solve a differential equation in a particular region enclosed by a Cauchy surface. John's equation sets consistency conditions for line integrals passing through the object, the line integrals corresponding to imaging energy passing through the object. Extrapolation is performed on the Cauchy data set to solve John's equation and determine missing cone beam data.

An exemplary embodiment of the system of the invention includes a source for applying imaging energy to the object. A detector detects imaging energy that has passed through the object. A positioner scans the object with the imaging energy such that the detector collects measured image data that constitutes a Cauchy data set for John's equation. An extrapolator extrapolates from the Cauchy data set to solve John's equation and determine missing cone beam data. An image supplier supplies an image of the object based on the measured image data and the determined missing cone beam data.

This technique has a number of advantages over the prior art. The scanning time (data acquisition time) and reconstruction time can be reduced. Errors in the data, particularly due to lag and signal to noise degradation with decreasing dose, can be minimized. The amount of measured data is minimized and this reduces the computational demands for image reconstruction process steps.

DETAILED DESCRIPTION OF THE INVENTION

Figure 1:
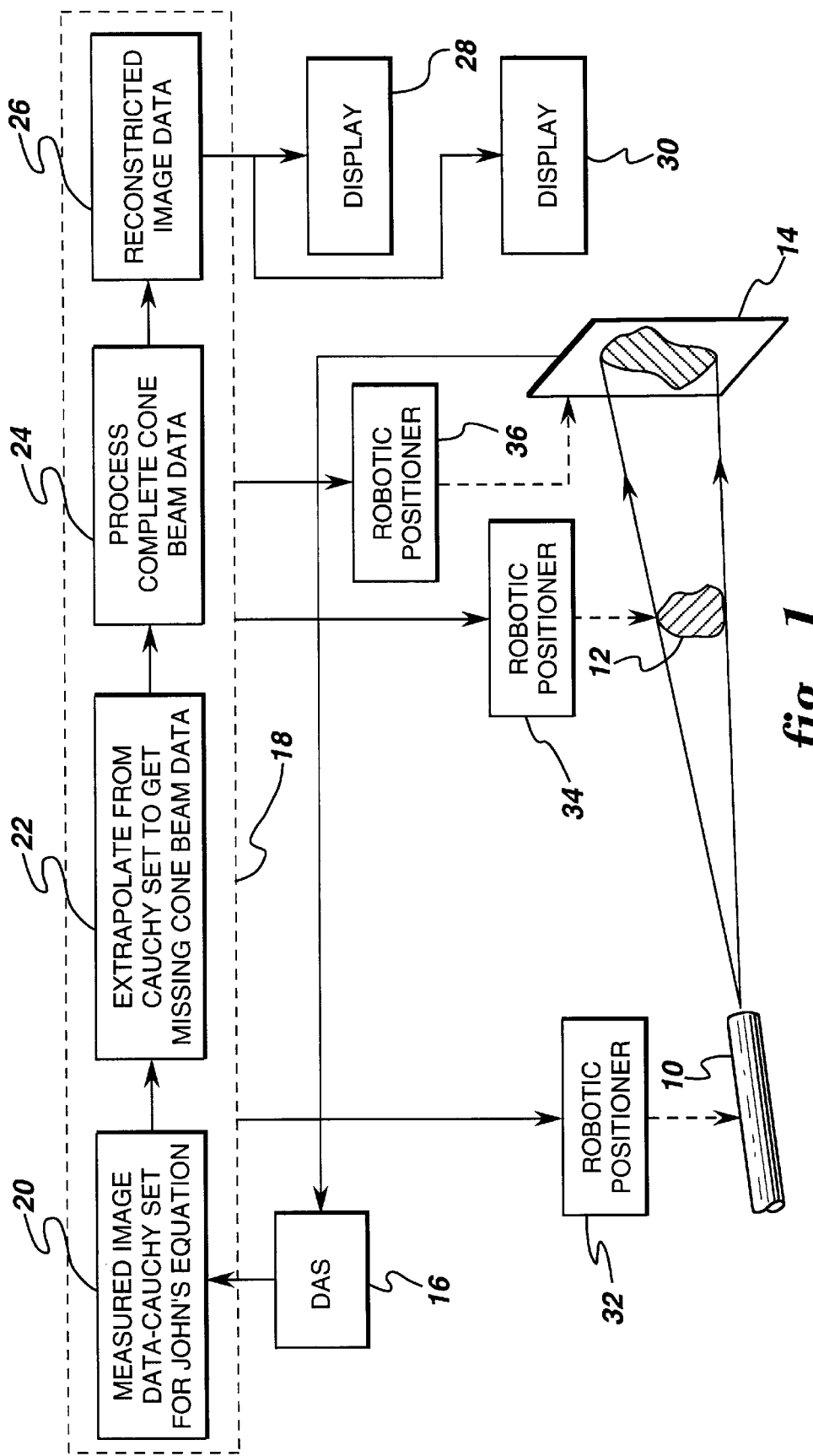
FIG. 1 is a simplified illustration of components of an imaging system and showing process steps within a processor.

Referring now to FIG. 1, imaging energy is applied by source 10 to object 12 and detected by detector 14. The source 10 can be a cone beam X-ray source, whereas the detector 14 can be an area detector such as a two dimensional array detector having an array of individual detector elements (separate elements not shown). The object 12 being imaged can be a patient, an industrial part, or other object being imaged using CT.

Cone beam energy that has passed through the object 12 is converted to corresponding electrical signals and sent to a data acquisition unit 16 that registers the electrical signals. Unit 16 in turn sends cone beam data to a processor 18, which can be a computer programmed to perform various process steps.

Various process steps performed in processor 18 are shown in simplified form in FIG. 1. At block 20, the measured image data provided is not a complete set for image reconstruction. However, the measured image data is a Cauchy data set for John's equation. A more detailed explanation of the significance of Cauchy data sets and John's equation follows below. At this stage, the Cauchy data set of measured data allows one to calculate missing cone beam data by extrapolation performed by the processor 18 at block 22. The measured data of block 20 and the missing cone beam data determined at block 22 together constitute a complete data set for exact reconstruction (i.e., meaning subject only to measurement errors and discretization errors). This complete data set of cone beam data, some measured and some extrapolated, is supplied to block 24 where processor 18 processes it in the usual fashion for cone beam data. For example, Radon derivative data is calculated followed by calculation of Radon data. Inverse Radon transformation may then be performed to provide reconstructed image data at block 26. The processing of the complete cone beam data may be, for example, as disclosed in the above listed Tam patent, which patent is hereby incorporated by reference. Regardless of whether that or another image reconstruction process from cone beam data is used, the block 26 operation of processor 18 supplies an image of the object (i.e., data corresponding to an image) that may be displayed by display 28, stored in a memory 30, or both.

The scanning trajectory will be defined by relative movements of the source 10, object 12, and detector 14 respectively controlled by robotic positioners 32, 34, and 36. Each of the robotic positioners 32, 34, and 36 causes relative scanning movement among the source 10, object 12, and detector 14. The positioners 32, 34, and 36 are in turn controlled by processor 18 to realize a scan trajectory satisfying criteria discussed below.

Although two or all three of the robotic positioners 32, 34, and 36 might be part of the imaging system of FIG. 1, only one of the three would usually be in a given system. For example, the positioner 32 could be used to determine a scan trajectory by moving source 10 relative to object 12 and detector 14, both of which remain stationary. In that example, there would not be positioners 34 and 36.

Figure 2:
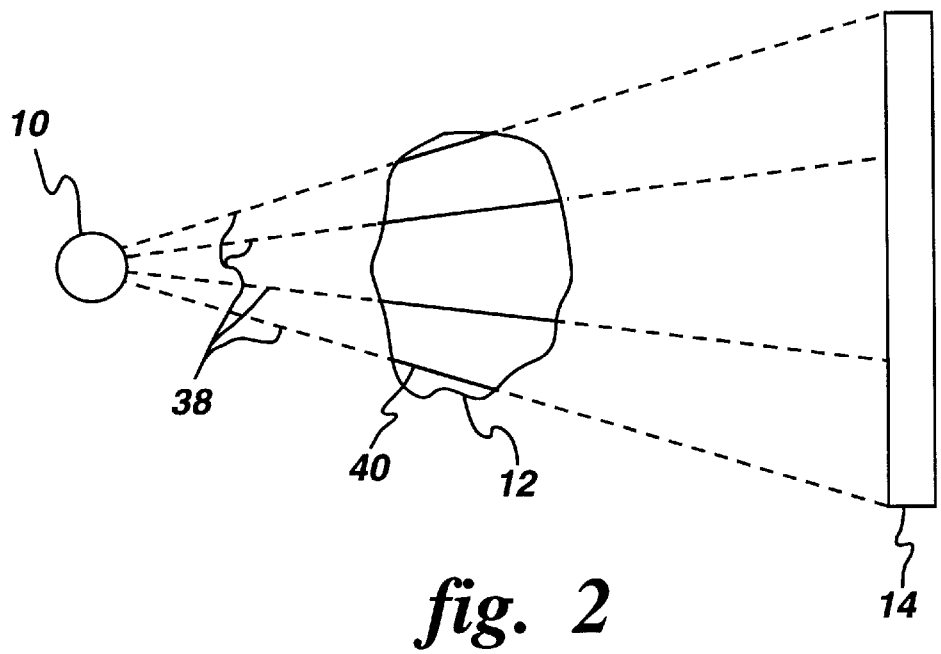
FIG. 2 is an illustration of some components of the imaging system and showing line integrals measured by the system.

FIG. 2 will be used to explain basic concepts used by the present invention before presenting more complex mathematical explanations. A source 10 is shown applying imaging energy beams 38 to pass through object 12 and strike the detector 14 (shown in side view). Four such energy beams 38 are shown for ease of illustration, but as readily appreciated the actual output of source 38 is a cone beam which may be considered as individual rays corresponding to the resolution of the area detector 14. In the simplified illustration, the detector 14 detects data corresponding to the four rays 38. Specifically, the data detected by detector 14 is dependent on line integrals 40 representative of the extent to which rays 38 are attenuated by passing through object 12.

One could measure a complete data set for exact reconstruction (i.e., providing a three-dimensional image) by measuring a sufficient set of line integrals 40 as source 10 is scanned in a trajectory. However, scanning in such a trajectory is complex and subject to other disadvantages.

Instead of measuring a complete data set by a complex scanning trajectory, the present technique is to obtain a data set corresponding to line integrals such as 40 where the data set is at least a minimal set of cone beam measurements such that missing cone beam data can be determined. The line integrals such as 40 must satisfy certain criteria that can be used to solve for missing cone beam data. Given a Cauchy data set for John's equation as explained in more detail below, one can solve John's equation and determine the missing cone beam data. A minimal amount of data for image reconstruction may thus be collected. This provides minimal scan and reconstruction times. Also, this reduces the X-ray dose to a patient when the object being imaged is a patient.

The space of lines in three real dimensions has greater dimension than the space in which the object being imaged sits. The present techniques are designed to take advantage of the overdeterminedness of the map taking an object to its line integrals by extrapolating the X-ray transform of the imaging object from a minimal cone beam data set of the object. This permits exact reconstruction (up to measurement and discretization errors) of the object being imaged. Furthermore, the reconstruction methods used are not predicated upon the specific extrapolation technique described below. The present technique works with a minimal cone beam data set (i.e., no more data than a Cauchy data set), but additional data can be measured to smooth noisy data in some instances such as imaging industrial parts.

Detailed Mathematics

The technique described below is designed to extrapolate almost everywhere the X-ray transform of an object from a minimal set of cone-beam measurements. The detailed mathematics is discussed below in the order of the following outline:

a. definition of the X-ray transform and its relationship to cone-beam data b. comparison of the "parameter counts" of possible density functions of the imaging object to that of the X-ray transform c. derivation of consistency conditions upon the X-ray transform (John's equation)

d. derivation of the fundamental solution to John's equation e. extrapolation of data, solution to the Cauchy problem via the fundamental solution to John's equation Points a, b, and c are simply the backdrop against which point d was developed. The invention uses the fundamental solution to John's equation to solve almost everywhere the Cauchy problem for the "rest" of the X-ray transform, meaning the missing cone beam data.

Definition of the X-ray Transform

After taking −ln (natural logarithm), the data we measure approximates line integrals of the imaging object. There are many ways to parametrize the space of lines in $R^3$. For our purposes, we first define the X-ray transform in terms of $\eta$, $\xi$, $\in R^3$, where $\eta \neq \xi$. We define the X-ray transform of a function, f, to be the line integral of f along the line through $\xi$ and $\eta$ and scaled as follows:

$$Xf(\xi, \eta) = \int_R f(\xi + t(\eta - \xi)) dt \qquad (0.1)$$

After taking −ln, the data that we measure is a normalized X-ray transform, where the direction vector is normalized to have length one.

$$X_N f(\xi, \eta) = \int_{\mathbb{R}} f(\xi + tu) dt \quad \text{where } u \equiv (\xi - \eta)/|\xi - \eta| \qquad (0.2)$$

$$= \int_{\mathbb{R}} f(\xi + (t/|\xi - \eta|)(\xi - \eta)) dt$$

$$= |\xi - \eta| \int_{\mathbb{R}} f(\xi + s(\xi - \eta)) ds$$

$$= |\xi - \eta| X f(\xi, \eta).$$

Parameter Count Comparison

Figure 3:
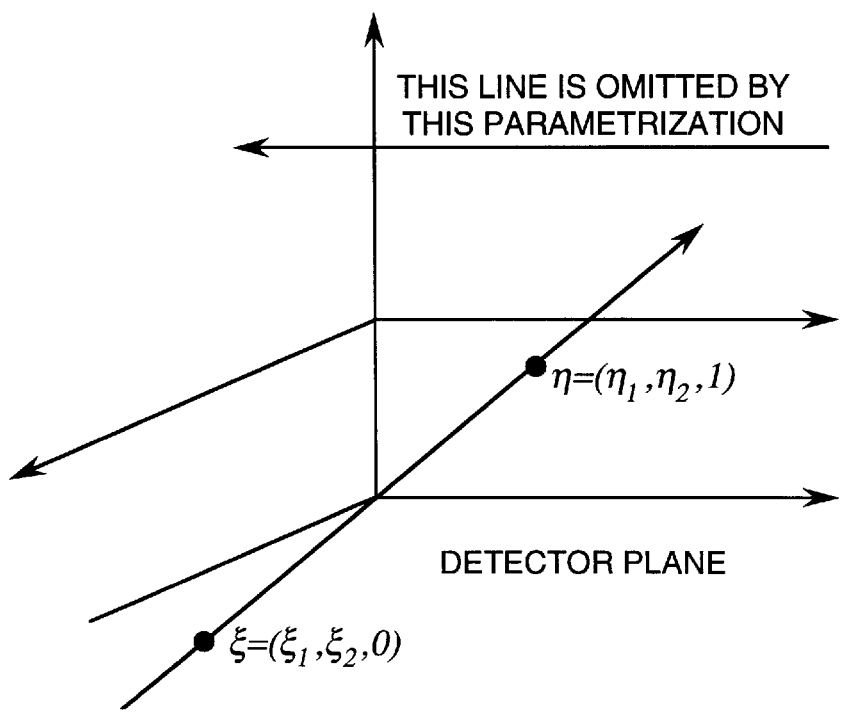
FIG. 3 shows a graph to illustrate mathematic concepts.

Notice that the X-ray transform can be specified almost everywhere with only four parameters. All lines in $\mathbb{R}^3$ except for horizontal lines can be specified by points $\xi$ such that $\xi_3=0$ and vectors $\eta$ such that $\eta_3=1$. See FIG. 3. X f($\xi;\eta$) integrates f along the line passing through $\xi$ and $\eta$. Note that almost all lines except for horizontal lines can be parametrized by $\xi$ lying in the plane defined by (z=0) and $\eta$ in the plane {z=1}.

This means that the X-ray transform is essentially a function of four variables, $\eta_1$, $\eta_2$, $\xi_1$, and $\xi_2$.

$$Xf(\xi_1, \xi_2, 0; (\eta - \xi)_1, (\eta - \xi)_2, 1) = \qquad (0.3)$$

$$\int_{\mathbb{R}} f((1-t)\xi_1 + t\eta_1, (1-t)\xi_2 + t\eta_2, t) dt$$

For sake of simplicity in deriving John's equation, assume that the function $f \in C_n^2(\mathbb{R}^3)$. Then $$X: f(x, y, z) \in C_0^2(\mathbb{R}^3) \to Xf(\xi_1, \xi_2, 0; \eta_1, \eta_2, 1) \in C_0^2(\mathbb{R}^4) \qquad (0.4)$$

The function f is dependent upon only three variables, whereas the function X f is written as a function of four variables. The mapping X is therefore overdetermined. This overdetermination is expressed in John's equation, a second order partial differential equation (PDE) satisfied by X f.

Derivation of John's Equation

For $f \in C_0^2(\mathbb{R}_3)$ we may differentiate X f with respect to $\eta_1$, $\eta_2$, $\xi_1$, and $\xi_2$.

$$Xf_{\eta_1} = \frac{\partial}{\partial \eta_1} \int_{\mathbb{R}} f((1-t)\xi_1 + t\eta_1, (1-t)\xi_2 + t\eta_2, t) dt \qquad (0.5)$$

$$= \int_{\mathbb{R}} t f_x((1-t)\xi_1 + t\eta_1, (1-t)\xi_2 + t\eta_2, t) dt$$

and $$Xf_{\eta_1,\xi_2} = \frac{\partial}{\partial \xi_2} \int_{\mathbb{R}} t f_x((1-t)\xi_1 + t\eta_1, (1-t)\xi_2 + t\eta_2, t) dt \qquad (0.6)$$

$$= \int_{\mathbb{R}} (1-t) t f_{x,y}((1-t)\xi_1 + t\eta_1, (1-t)\xi_2 + t\eta_2, t) dt$$

Similarly, $$Xf_{\eta_2,\xi_1} = \int_{\mathbb{R}} (1-t) t f_{y,x}((1-t)\xi_1 + t\eta_1, (1-t)\xi_2 + t\eta_2, t) dt \qquad (0.7)$$

$$= \int_{\mathbb{R}} (1-t) t f_{x,y}((1-t)\xi_1 + t\eta_1, (1-t)\xi_2 + t\eta_2, t) dt$$

John's equation is simply $$Xf_{\eta_1,\xi_2} = Xf_{\eta_2,\xi_1} \qquad (0.8)$$

Note that in this particular case with $\epsilon=0$ and $\eta_3=1$ only 0.8 is relevant. Generally, however, the same derivation results in a system of three PDEs of the form 0.8. This applies to cone-beam data in that $$\left( \frac{\partial^2}{\partial \xi_1 \partial \eta_2} - \frac{\partial^2}{\partial \xi_2 \partial \eta_1} \right) \left( \frac{X_N f(\xi_1, \xi_2, 0; \eta_1, \eta_2, 1)}{\sqrt{(\eta_1 - \xi_1)^2 + (\eta_2 - \xi_2)^2 + 1}} \right) = 0 \qquad (0.9)$$

In the next section we will derive the fundamental solution to 0.8 and in the subsequent section use this fundamental solution for $\underline{X}_N \underline{f}$ given only measurement of $X_N$ f on a $|\xi-\eta|$ noncharacteristic surface of 0.8.

Derivation of the Fundamental Solution to John's Equation

Since John's equation is a constant coefficient PDE, we compute its fundamental solution using Fourier transforms. The fundamental solution satisfies $$\delta(\xi_1, \xi_2, \eta_1, \eta_2) = \left( \frac{\partial^2}{\partial \xi_1 \partial \eta_2} - \frac{\partial^2}{\partial \xi_2 \partial \eta_1} \right) u(\xi_1, \xi_2; \eta_1, \eta_2) \qquad (0.10)$$

We take as dual variables x and y, where x, y, $\xi$, $\eta \in \mathbb{R}^2$ $\xi \sim x$ and $\eta \sim y$ The inverse transform of 0.10 is $$1 = \bar{\delta}(x_1, x_2, y_1, y_2) \qquad (0.11)$$

$$= \int_{\mathbb{R}^4} \left( \frac{\partial^2}{\partial \xi_1 \partial \eta_2} - \frac{\partial^2}{\partial \xi_2 \partial \eta_1} \right) u(\xi; \eta) e^{2\pi i (x \cdot \xi + y \cdot \eta)} d\xi d\eta$$

$$= \int_{\mathbb{R}^4} ((-2\pi i) x_1 u_{\eta_2} - (-2\pi i) x_2 u_{\eta_1}) e^{2\pi i (x \cdot \xi + y \cdot \eta)} d\xi d\eta$$

$$= \int_{\mathbb{R}^4} ((-2\pi i)^2 y_2 x_1 u - (-2\pi i)^2 y_1 x_2 u) e^{2\pi i (x \cdot \xi + y \cdot \eta)} d\xi d\eta$$

$$= (-2\pi i)^2 (y_2 x_1 - y_1 x_2) \int_{\mathbb{R}^4} u e^{2\pi i (x \cdot \xi + y \cdot \eta)} d\xi d\eta$$

$$= -4\pi^2 (x \times y) \check{u}(x, y)$$

To solve for u=u ($\xi$; $\eta$) we must solve 0.11 for u and take its Fourier transform. Although this is conceptually clear to those trained in Fourier analysis, the details are carried out for clarity below. Before beginning, define $\Theta_v$=angle between vector $v \in \mathbb{R}^2$ and $e_1=(1,0)$ $$x = \tau\alpha \text{ where } \tau \in \mathbb{R}, \quad \alpha \in \mathbb{R}^2 \qquad (0.12)$$

$y = s\beta$ where $s \in \mathbb{R}, \quad \beta \in \mathbb{R}^2$ $\alpha = (\cos\theta_\alpha, \sin\theta_\alpha)$ $\beta = (\cos\theta_\beta, \sin\theta_\beta)$ Using this notation we compute the Fourier transform of u in polar coordinates $$u(\xi; \eta) = \hat{u}^\wedge(\xi; \eta) \qquad (0.13)$$

$$= \frac{-1}{4\pi^2} \int_{\mathbb{R}^2} \int_{\mathbb{R}^2} \frac{1}{x_1 y_2 - x_2 y_1} e^{-2\pi i (x \cdot \xi + y \cdot \eta)} dx dy$$

$$= \frac{-1}{4\pi^2} \int_0^\pi \int_{\mathbb{R}} \int_0^\pi \int_{\mathbb{R}} \frac{1}{\tau s \sin(\theta_\beta - \theta_\alpha)} e^{-2\pi i \tau (\alpha \cdot \xi)}$$

-continued $$e^{-2\pi i s(\beta \cdot \eta)} \tau s d\tau d\theta_\alpha d s d\theta_\beta$$

$$= \frac{-1}{4\pi^2} \int_0^\pi \int_0^\pi \frac{1}{\sin(\theta_\beta - \theta_\alpha)} \left( \int_R e^{-2\pi i \tau(\alpha \cdot \xi)} d\tau \right)$$

$$\left( \int_R e^{-2\pi i s(\beta \cdot \eta)} ds \right) d\theta_\alpha d\theta_\beta$$

$$= \frac{-1}{4\pi^2} \int_0^\pi \int_0^\pi \frac{1}{\sin(\theta_s - \theta_\alpha)} \delta(\alpha \cdot \xi) \delta(\beta \cdot \eta) d\theta_\alpha d\theta_\beta$$

In order to evaluate 0.13 we make more changes of variables $$\sigma = |\xi| \cos(\Theta_\alpha - \Theta_\xi)$$

$$d\sigma = -|\xi| \sin(\Theta_\alpha - \Theta_\xi) d\Theta_\alpha$$

$$\Theta_a = \Theta_\xi - \cos^{-1}(\sigma/|\xi|)$$

$$\sigma \in |\xi|(-\cos(\Theta_\xi), \cos(\Theta_\xi)) \qquad (0.14)$$

and $$\tau = |\eta| \cos(\Theta_\beta - \Theta_\eta)$$

$$d\tau = -|\eta| \sin(\Theta_\beta - \Theta_\eta) d\Theta_\beta$$

$$\Theta_\beta = \Theta_\eta - \cos^{-1}(\tau/|\eta|)$$

$$\tau \in |\eta|(-\cos(\Theta_\eta), \cos(\Theta_\eta)) \qquad (0.15)$$

Combining 0.13, 0.14, and 0.15, we get:

$$u(\xi; \eta) = \frac{-1}{4\pi^2} \int_{-|\eta|\cos\theta_\eta}^{|\eta|\cos\theta_\eta} \int_{-|\xi|\cos\theta_\xi}^{|\xi|\cos\theta_\xi} \frac{\delta(\sigma)\delta(\tau) d\sigma d\tau}{\sin\left(\theta_\eta - \theta_\xi + \cos^{-1}\left(\frac{\tau}{|\eta|}\right) - \cos^{-1}\left(\frac{\sigma}{|\xi|}\right)\right) \sqrt{|\xi|^2 - \sigma^2} \sqrt{|\eta|^2 - \tau^2}}$$

$$= \frac{-1}{4\pi^2 |\xi||\eta|\sin(\theta_\eta - \theta_\xi + \cos^{-1}(0) - \cos^{-1}(0))}$$

Note first that the denominator is multiple valued, and secondly that u is inversely proportional to the cross products of the vectors $\xi$ and $\eta$. We choose the sign of the denominator so that $$u(\xi; \eta) = \frac{1}{4\pi^2(\xi \times \eta)} = \frac{1}{4\pi^2(\xi_1 \eta_2 - \xi_2 \eta_1)} \qquad (0.16)$$

To verify that u is in fact a fundamental solution of John's equation we must verify that u satisfies John's equation away from the origin and that $$1 = \int_{R^2} \int_{R^2} \left( \frac{\partial^2}{\partial \xi_1 \partial \eta_2} - \frac{\partial^2}{\partial \xi_2 \partial \eta_1} \right) u(\xi_1, \xi_2, \eta_1, \eta_2) d\xi d\eta \qquad (0.17)$$

These facts can be easily verified, but need not be included here.

Extrapolation of Data—Solution to the Cauchy Problem

Given a fundamental solution to a PDE, solution of the Cauchy problem is well documented. In this section, we consider a special, but practical case shown in FIG. 4 satisfying the following criterion:

1. the imaging object has finite size and lies between the planes z=0 and z=1

2. the source moves along the circular path or, more specifically on a path $\eta_3 = 1$, $\eta^{2/1} + \eta^{2/2} = 1$ 3. the cone beam envelopes the imaging object 4. the detector is large enough to detect all radiation which has passed through the object (it may lie in the plane $\xi_3 = 0$)

For simplicity of notation, write for $\xi, \eta \in R^2$ $$d(\xi; \eta) \equiv Xf(\xi, \eta) = \frac{X_N f(\xi, \eta)}{\sqrt{|\xi - \eta|^2 + 1}}$$

and recall that we measure $X_N$ and can easily compute $|\xi - \eta|$. Therefore, it is sufficient to extrapolate $d(\xi; \eta)$. Under these conditions we can extrapolate d in $\Omega$ from the data measured on the boundary $d\Omega$ if $d\Omega$ is noncharacteristic. (See equation 1.3) First define:

$$D(\alpha, \beta) = (d_{\beta_2}, -d_{\beta_1}, -d_{\alpha_2}, d_{\alpha_1})$$

$$U(\alpha, \beta) = (u_{\beta_2}, -u_{\beta_1}, -u_{\alpha_2}, u_{\alpha_1}) = \frac{(\alpha_1, \alpha_2, \beta_1, \beta_2)}{4\pi^2(\alpha \times \beta)^2}$$

We can rewrite John's equation in this notation as $$\tfrac{1}{2} \nabla \cdot D(\alpha, \beta) = d_{\beta_2, \alpha_1} - d_{\beta_1, \alpha_2} = 0$$

For $(\eta, \xi) \in \Omega$ we can compute $d(\xi; \eta)$ as follows:

$$d(\xi; \eta) = (d * \delta)(\xi; \eta) \qquad (18)$$

$$= \int_\Omega d(\alpha, \beta) \delta(\xi - \alpha; \eta - \beta) d\alpha \, d\beta$$

$$= \int_\Omega d(\alpha, \beta)(u_{\eta_2, \xi_1} - u_{\eta_1, \xi_2})(\xi - \alpha; \eta - \beta) d\alpha \, d\beta$$

$$= \frac{1}{2} \int_\Omega d(\alpha \cdot \beta) \nabla \cdot U(\xi - \alpha; \eta - \beta) d\alpha \, d\beta$$

$$= \frac{1}{2} \int_\Omega \nabla : (d(\alpha, \beta) U(\xi - \alpha; \eta - \beta)) -$$

$$\nabla d(\alpha, \beta) \cdot U(\xi - \alpha; \eta - \beta) d\alpha \, d\beta$$

$$= \frac{1}{2} \int_{d\Omega} d(\alpha, \beta) n \cdot U(\xi - \alpha; \eta - \beta)) d\alpha \, d\beta$$

$$\frac{1}{2} \int_\Omega \nabla d(\alpha, \beta) \cdot U(\xi - \alpha; \eta - \beta) d\alpha \, d\beta$$

This can be simplified further, by noting:

$$n \cdot U(\xi - \alpha; \eta - \beta) = \frac{2(\alpha \times \beta) - (\xi \times \beta) - (\alpha \times \eta)}{4\pi^2 \sqrt{|\alpha|^2 + |\beta|^2} \left[(\xi - \alpha) \times (\eta - \beta)\right]^2} \quad (19)$$

$$\nabla d(\alpha, \beta) \cdot U(\xi - \alpha; \eta - \beta) = D(\alpha, \beta) \cdot \nabla u(\xi - \alpha; \eta - \beta)$$

$$\nabla \cdot D(\alpha, \beta) = 0$$

Plugging these identities into the second integral in 6.1 we get $$\int_\Omega \nabla d(\alpha, \beta) \cdot U(\xi - \alpha; \eta - \beta) d\alpha d\beta = \quad (20)$$

$$\int_\Omega D(\alpha, \beta) \cdot \nabla u(\xi - \alpha; \eta - \beta) d\alpha d\beta =$$

$$\int_\Omega \nabla \cdot (D(\alpha, \beta) u(\xi - \alpha; \eta - \beta)) -$$

$$u(\xi - \alpha; \eta - \beta) \nabla \cdot D(\alpha, \beta) d\alpha d\beta =$$

$$\int_{d\Omega} n \cdot D(\alpha, \beta) u(\xi - \alpha; \eta - \beta) d\alpha d\beta$$

Plugging 6.3 and the definition of u into 6.1 we get the solution to the Cauchy problem. For $(\xi, \eta) \in \Omega$, $d(\xi, \eta)$ is a weighted integral of d and its derivatimes on $\partial\Omega$.

$$d(\xi; \eta) = \quad (6.3)$$

$$\frac{1}{8\pi^2} \int_{d\Omega} n \cdot \left[ d(\alpha, \beta) U((\xi - \alpha), (\eta - \beta)) - \frac{D(\alpha, \beta)}{(\xi - \alpha) \times (\eta - \beta)} \right] d\alpha \, d\beta$$

Figure 4:
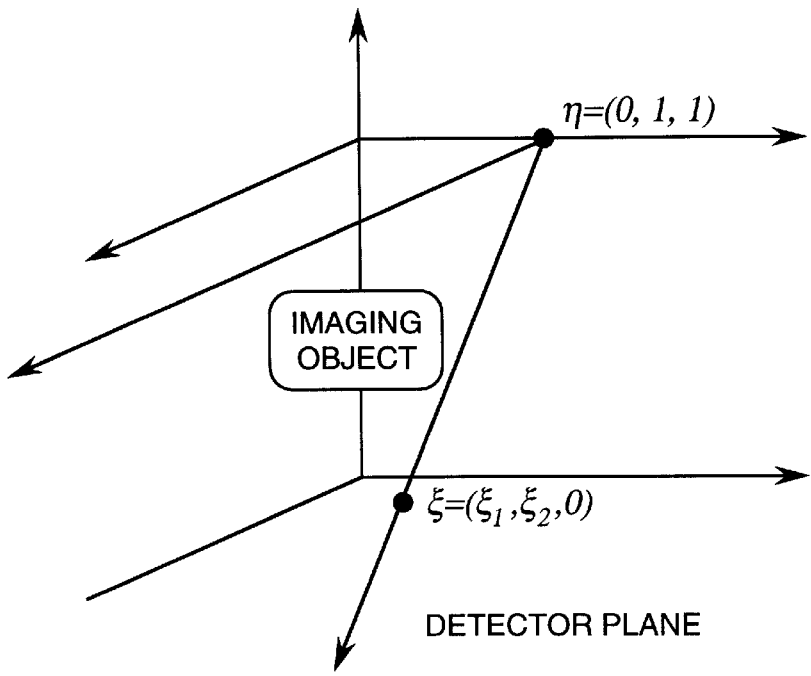
FIG. 4 shows the geometry of a particular source trajectory.

FIG. 4 shows the geometry of the particular source trajectory for which John's equation is derived and data can be extrapolated.

Figure 5:
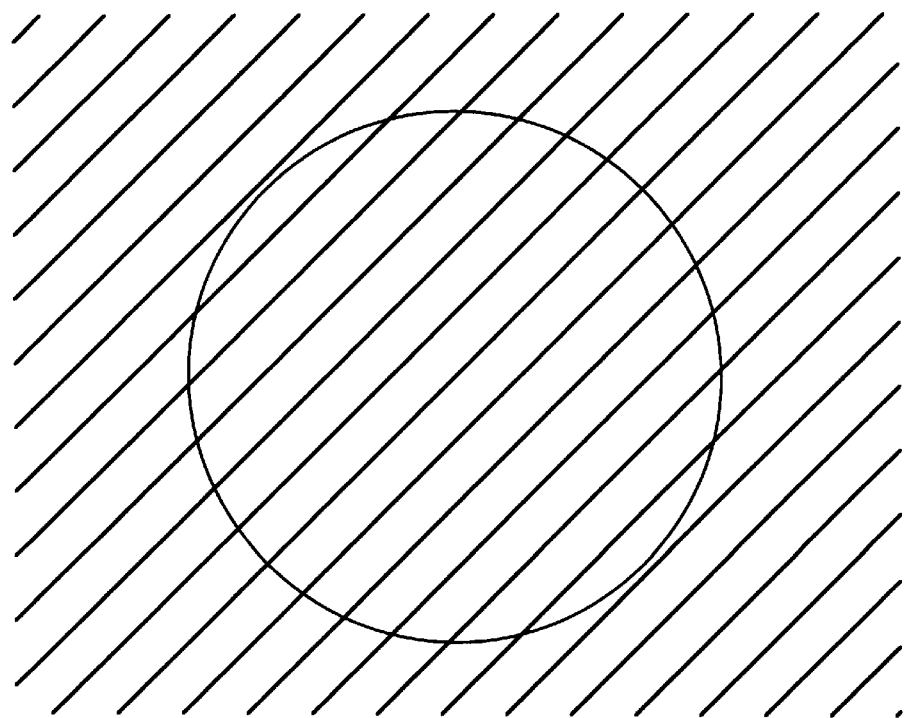
FIG. 5 is a planar view of the source trajectory of FIG. 5 illustrating locations corresponding to extrapolated data.

FIG. 5 shows source positions and corresponding extrapolated data corresponding to FIG. 4. This is a view of the plane in which the source trajectory lies. The source moves along a circular path. Extrapolated data is data that could have also been measured from source positions within the circular source trajectory. Note that data extrapolation is not predicated upon a circular source trajectory.

Suitable Cauchy surfaces should be identified, not only for the well-posed boundary value problem, but also for the practical constraints that come with data generated using a point source and measured by a flat panel area detector. The symbol for John's equation is:

$$\Lambda(\xi,\eta) = \xi_1\eta_2 - \xi_2\eta_1 \quad \text{Equation (0.21)}$$

If the function $\phi = \phi(\epsilon, \eta)$ define the surface $\partial\Omega$, then the criteria for $\partial\Omega$ to be noncharacteristic is that $$\Lambda(\nabla\phi) \neq 0 \quad \text{Equation (0.22)}$$

When $\phi(\epsilon, \eta) = \epsilon_1\eta_2 - \epsilon_2\eta_1 - 1$ then $$\Lambda(\nabla\phi) = 1 \quad \text{Equation (0.23)}$$

If this formulation for an can be used in equation 0.20 (despite the fact that $\Omega$ is not a domain in $\mathbb{R}^4$, the solution for d(0,0) is:

$$d(0, 0) = \quad \text{Equation (0.24)}$$

$$\frac{-1}{8\pi^2} \int_{\alpha \times \beta} n \cdot [d(\alpha, \beta)(\alpha_1, \alpha_2, \beta_1, \beta_2) + D(\alpha, \beta)] dS_{urface}$$

This solution to the Dirichlet problem does not require any derivatives of the measured data. The solution to the more general Cauchy problem, however, does require differentiation of the data.

Consistency conditions upon cone beam data can be derived for any source trajectory and can be solved for any trajectory generating Cauchy data on a non-characteristic surface. To date, the simplest geometry found for data extrapolation appears to be that shown above. However, the technique extends to more general geometries. In the case of an unbounded object (in the CT sense) which is not enveloped by the cone beam, additional measures will be required. It may well be sufficient to augment the missing line integrals corresponding to source positions on the source trajectory with data satisfying integral conditions upon Cauchy data. This data will not necessarily be correct for the given imaging object, but should provide a physical data set which can be used by the extrapolation procedure described above. As the errors in resulting reconstructions can lie as far as the field of view as do the incorrect Cauchy data/line integrals, such errors are acceptable in some situations.

I claim:

1. A method of imaging an object comprising the steps of:
   applying imaging energy from a source to the object;
   detecting imaging energy that has passed through the object by use of a detector;
   scanning the object with the imaging energy such that the detector collects measured image data that constitutes a Cauchy data set for John's equation;
   extrapolating from the Cauchy data set to solve John's equation and determine missing cone beam data; and
   supplying an image of the object based on the measured image data and the determined missing cone beam data.

2. The method of claim 1 wherein the image of the object is an exact reconstruction of the object up to measurement and discretization errors.

3. The method of claim 2 wherein the measured image data and the determined missing cone beam data together constitute a complete data set for image reconstruction purposes.

4. The method of claim 3 wherein the detector is an area detector and the source is a point source.

5. The method of claim 4 wherein the scanning step is accomplished by moving the source in a scanning trajectory relative to the object.

6. The method of claim 4 wherein the scanning step is accomplished by moving the object in a scanning trajectory relative to the source.

7. The method of claim 4 wherein the scanning step uses a circular scanning trajectory and the missing cone beam data determined by the extrapolating step includes data corresponding to points interior to the circular scanning trajectory.

8. The method of claim 4 wherein the scanning step uses a scanning trajectory with some portions lying in a plane and the missing cone beam data determined by the extrapolating step includes data corresponding to points in the plane.

9. The method of claim 1 wherein the measured image data and the determined missing cone beam data together constitute a complete data set for image reconstruction purposes, the detector is an area detector, and the source is a point source.

10. The method of claim 1 wherein the extrapolation step determines missing data from within a region based on data measured at the boundary of the region.

11. A system for imaging an object comprising:
   a source for applying imaging energy to the object;
   a detector for detecting imaging energy that has passed through the object;
   a positioner scanning the object with the imaging energy such that the detector collects measured image data that constitutes a Cauchy data set for John's equation;
   an extrapolator extrapolating from the Cauchy data set to solve John's equation and determine missing cone beam data; and
   an image supplier supplying an image of the object based on the measured image data and the determined missing cone beam data.

12. The system of claim 11 wherein the image of the object is an exact reconstruction of the object up to measurement and discretization errors.

13. The system of claim 12 wherein the measured image data and the determined missing cone beam data together constitute a complete data set for image reconstruction purposes.

14. The system of claim 13 wherein the detector is an area detector and the source is a point source.

15. The system of claim 14 wherein the positioner moves the source in a scanning trajectory relative to the object.

16. The system of claim 14 wherein the positioner moves the object in a scanning trajectory relative to the source.

17. The system of claim 14 wherein the positioner provides a circular scanning trajectory and the extrapolator determines missing cone beam data including data corresponding to points interior to the circular scanning trajectory.

18. The system of claim 14 wherein the positioner provides a scanning trajectory with some portions lying in a plane and the missing cone beam data determined by the extrapolator includes data corresponding to points in the plane.

19. The system of claim 11 wherein the measured image data and the determined missing cone beam data together constitute a complete data set for image reconstruction purposes, the detector is an area detector, and the source is a point source.

20. The system of claim 11 wherein the extrapolator determines missing data from within a region based on data measured at the boundary of the region.

* * * * *